(12) United States Patent
Tavassi et al.

(10) Patent No.: US 12,303,547 B2
(45) Date of Patent: May 20, 2025

(54) COMPOUND, USE, PHARMACEUTICAL COMPOSITION, METHOD OF DIAGNOSIS, METHOD OF TREATMENT, AND METHOD OF TRANSPORTATION AND/OR INTERNALIZATION OF A COMPOUND INTO EUKARYOTIC CELLS

(71) Applicant: INSTITUTO BUTANTAN, São Paulo (BR)

(72) Inventors: Ana Marisa Chudzinski Tavassi, SãPaulo (BR); Miryam Paola Alvarez-Flores, São Paulo (BR); Katia Luciano Pereira Morais, São Paulo (BR); Gilles Mourier, Villebon-sur-Yvette (FR); Denis Servent, Gif sur Yvette (FR)

(73) Assignee: INSTITUTO BUTANTAN, São Paulo (BR)

( * ) Notice: Subject to any disclaimer, the term of this patent is extended or adjusted under 35 U.S.C. 154(b) by 494 days.

(21) Appl. No.: 17/309,373

(22) PCT Filed: Nov. 22, 2019

(86) PCT No.: PCT/BR2019/050501
§ 371 (c)(1),
(2) Date: May 21, 2021

(87) PCT Pub. No.: WO2020/102874
PCT Pub. Date: May 28, 2020

(65) Prior Publication Data
US 2022/0088122 A1    Mar. 24, 2022

(30) Foreign Application Priority Data

Nov. 22, 2018 (BR) .......................... 102018074037-7

(51) Int. Cl.
*A61K 38/17* (2006.01)
*A61K 38/10* (2006.01)
*A61K 47/60* (2017.01)

(52) U.S. Cl.
CPC .............. *A61K 38/17* (2013.01); *A61K 38/10* (2013.01); *A61K 47/60* (2017.08)

(58) Field of Classification Search
CPC ........ A61P 35/00; A61P 7/02; C07K 14/8114; C07K 14/43527; A61K 38/00
See application file for complete search history.

(56) References Cited

U.S. PATENT DOCUMENTS 8,883,740 B2   11/2014   De Souza Ventura et al.
2009/0042786 A1*  2/2009  Maria ..................... A61P 41/00
                                                                    435/325

FOREIGN PATENT DOCUMENTS

| CA | 2712807 C | 5/2019 | |
| WO | WO2006029492 A1 * | 3/2006 | .......... C07K 14/435 |
| WO | 2008109976 A1 | 9/2008 | |

OTHER PUBLICATIONS

Chudzinski-Tavassi et al. C-terminal domain is responsible for a Kunitz-type inhibitor uptake by tumor cells. Experimental Biology 2018 Meeting Abstract; The FASEB Journal/vol. 32, Issue S1/p. lb188-lb188. (Year: 2018).*
Kristensen et al. Applications and Challenges for Use of Cell-Penetrating Peptides as Delivery Vectors for Peptide and Protein Cargos. Int. J. Mol. Sci. 2016, 17, 185; doi: 10.3390. (Year: 2016).*
Akagi et al., "Pro-apoptotic effects of Amblyomin-X in murine renal cell carcinoma in vitro", Biomedicine & Pharmacotherapy, vol. 66, pp. 64-69, 2012.
Akagi et al., "Corrigendum to "Pro-apoptotic effects of Amblyomin-X in murine renal cell carcinoma" in vitro", Biomedicine & Pharmacotherapy, vol. 118, 1 pages, 2019.
Alvarez Flores et al., "Losac, a factor X activator from Lonomia obliqua bristle extract: Its role in the pathophysiological mechanisms and cell survival", Biochemical and Biophysical Research Communications, vol. 343, pp. 1216-1223, 2006.
Batista et al., "A new Factor Xa inhibitor from Amblyomma cajennense with a unique domain composition", Archives of Biochemistry and Biophysics, vol. 493, pp. 151-156, 2010.
Benavent Acero et al., "Mechanisms of Cellular Uptake, Intracellular Transportation, and Degradation of CIGB-300, a Tat-Conjugated Peptide, in Tumor Cell Lines", Molecular Pharmaceutics, 10 pages, Apr. 16, 2014.
Benedetti et al., "Bothrops jararaca Peptide with Anti-Hypertensive Action Normalizes Endothelium Dysfunction Involved in Physiopathology of Preeclampsia", PLoS One, vol. 6, Issue 8, 7 pages, Aug. 2011.
Böhm et al., "Quantitative analysis of protein far UV circular dichroism spectra by neural networks", Protein Engineering, vol. 5, No. 3, pp. 191-195, 1992.
Carrijo-Carvalho et al., "A Lipocalin-Derived Peptide Modulating Fibroblasts and Extracellular Matrix Proteins", Journal of Toxicology, vol. 2012. Art. ID. 325250. 8 pages, 2012.
Chudzinski-Tavassi et al., "A new tick Kunitz type inhibitor, Amblyomin-X, induces tumor cell death by modulating genes related to the cell cycle and targeting the ubiquitin-proteasome system", Toxicon, vol. 56, pp. 1145-1154, 2010.

(Continued)

*Primary Examiner* — Aradhana Sasan
*Assistant Examiner* — Jia-Hai Lee
(74) *Attorney, Agent, or Firm* — McKee, Voorhees & Sease, PLC

(57) ABSTRACT

The invention pertains to the technical fields of pharmaceutical sciences, immunology, diagnosis and/or treatment of cancer. Specifically, the invention relates to peptides derived from the C-terminal portion of the tick amblyomin-X protein, said peptides being intended for targeting or promoting the internalization of molecular entities into the intracellular domain of eukaryotic or neoplastic cells. The invention also relates to the use of said peptides for modifying other pharmaceutically active ingredients, to a pharmaceutical composition comprising said peptides and to a method of diagnosis, prognosis and/or treatment of cancer or other cell-altering conditions.

11 Claims, 15 Drawing Sheets
(1 of 15 Drawing Sheet(s) Filed in Color)
Specification includes a Sequence Listing.

(56) References Cited

OTHER PUBLICATIONS

Chudzinski-Tavassi et al., "C-terminal domain is responsible for a Kunitz-type inhibitor uptake by tumor cells", The FASEB Journal, vol. 32, Issue 51, 2 pages, Apr. 1, 2018.
Chudzinski-Tavassi et al., "Tick salivary gland as potential natural source for the discovery of promising antitumor drug candidates", Biomedicine & Pharmacotherapy, vol. 77, pp. 14-19, 2016.
Chudzinski-Tavassi et al., "A lipocalin sequence signature modulates cell survival", FEBS Letters, vol. 584, pp. 2896-2900, 2010.
De Souza et al., "Promising pharmacological profile of a Kunitz-type inhibitor in murine renal cell carcinoma model", Oncotarget, vol. 7, No. 38, pp. 62255-62266, Aug. 23, 2016.
Deleage et al., "An interactive graphic program for calculating the secondary structure content of proteins from circular dichroism spectrum", Cabios, vol. 9, No. 2, pp. 197-199, 1993.
Jaffe et al., "Culture of Human Endothelial Cells Derived from Umbilical Veins: Identification by Morphologic and Immunologic Criteria, The Journal of Clinical Investigation, vol. 52, pp. 2745-2756,", Nov. 1973.
Kristensen et al., "Applications and Challenges for Use of Cell-Penetrating Peptides as Delivery Vectors for Peptide and Protein Cargos", International Journal of Molecular Sciences, 17 p. Jul. 30, 2016.
Morais et al., "Amblyomin-X induces ER stress, mitochondrial dysfunction, and caspase activation in human melanoma and pancreatic tumor cell, Mol. Cell Biochem.," vol. 415, pp. 119-131, 2016.
Pacheco et al., "Dynein Function and Protein Clearance Changes in Tumor Cells Induced by a Kunitz-Type Molecule, Amblyomin-X", PLoS One, 20 pages, Dec. 5, 2014.
Pacheco et al., "Specific role of cytoplasmic dynein in the mechanism of action of an antitumor molecule, Amblyomin-X", Experimental Cell Research, vol. 340, pp. 248-258, 2016.
Perea et al., "Antitumor Effect of a Novel Proapoptotic Peptide that Impairs the Phosphorylation by the Protein Kinase 2 (Casein KInase 2)", Cancer Research, vol. 64, pp. 7127-7129, Oct. 1, 2004.
Perera et al., "Sensitivity of tumor cells towards CIGB-300 anticancer peptide relies on its nucleolar localization", Journal of Peptide Science, vol. 18, pp. 215-223, 2012.
Riedl et al., "In search of a novel target—Phosphatidylserine exposed by non-apoptotic tumor cells and metastases of malignancies with poor treatment efficacy", Biochimica et Biophysica Acta, vol. 1808, pp. 2638-2645, 2011.
Schmidt et al., "Amblyomin-X, a recombinant Kunitz-type inhibitor, regulates cell adhesion and migration of human tumor cells", Cell Adhesion & Migration, vol. 14, No. 1, pp. 129-138, 2020.
Ventura et al., "A Kunitz-type FXa inhibitor affects tumor progression, hypercoagulable state and triggers apoptosis", Biomedicine & Pharmacotherapy, vol. 67, pp. 192-196, 2013.

* cited by examiner

P15-Cter: CWMSPRHLGTCEEQTHFHFESPKLISFKVQDYWILNDIMKKNLTGISLKSEEEDADSGEID

Fig. 11

Amblyomin-X

C-Terminal

MRQLAVLALVFTSMCVCGSANSKASCRLPSLAQDETCSIATERRWYYNGTACEAFIFGCGGNDNNFDRVEGCQRLSEQTHFHFESPKLICFKVQDYWLNDMKKNLTGISLKSEEEDADSGEID

Kunitz Domain

F1C-FITC     F2C-FITC     F3C-FITC

EEQTHFHFESPKLICFKVQDYWILNDMKKNLTGISLKSEEEDADSGEID

Fig. 13

SEQUENCE LISTING

```
<160> NUMBER OF SEQ ID NOS: 8

<210> SEQ ID NO 1
<211> LENGTH: 50
<212> TYPE: PRT
<213> ORGANISM: Artificial sequence
<220> FEATURE:
<223> OTHER INFORMATION: synthetic

<400> SEQUENCE: 1

Glu Glu Gln Thr His Phe His Phe Glu Ser Pro Lys Leu Ile Ser Phe
1               5                   10                  15

Lys Val Gln Asp Tyr Trp Ile Leu Asn Asp Ile Met Lys Lys Asn Leu
            20                  25                  30

Thr Gly Ile Ser Leu Lys Ser Glu Glu Asp Ala Asp Ser Gly Glu
        35                  40                  45

Ile Asp
    50

<210> SEQ ID NO 2
<211> LENGTH: 11
<212> TYPE: PRT
<213> ORGANISM: Artificial sequence
<220> FEATURE:
<223> OTHER INFORMATION: synthetic

<400> SEQUENCE: 2

Tyr Ala Ile Gly Tyr Ser Ser Lys Asp Tyr Lys
1               5                   10

<210> SEQ ID NO 3
<211> LENGTH: 61
<212> TYPE: PRT
<213> ORGANISM: Artificial sequence
<220> FEATURE:
<223> OTHER INFORMATION: synthetic

<400> SEQUENCE: 3

Tyr Ala Ile Gly Tyr Ser Ser Lys Asp Tyr Lys Glu Glu Gln Thr His
1               5                   10                  15

Phe His Phe Glu Ser Pro Lys Leu Ile Ser Phe Lys Val Gln Asp Tyr
            20                  25                  30

Trp Ile Leu Asn Asp Ile Met Lys Lys Asn Leu Thr Gly Ile Ser Leu
        35                  40                  45

Lys Ser Glu Glu Glu Asp Ala Asp Ser Gly Glu Ile Asp
    50                  55                  60

<210> SEQ ID NO 4
<211> LENGTH: 11
<212> TYPE: PRT
<213> ORGANISM: Artificial sequence
<220> FEATURE:
<223> OTHER INFORMATION: synthetic
```

<400> SEQUENCE: 4

Cys Trp Met Ser Pro Arg His Leu Gly Thr Cys
1               5                   10

<210> SEQ ID NO 5
<211> LENGTH: 61
<212> TYPE: PRT
<213> ORGANISM: Artificial sequence
<220> FEATURE:
<223> OTHER INFORMATION: synthetic

<400> SEQUENCE: 5

Cys Trp Met Ser Pro Arg His Leu Gly Thr Cys Glu Glu Gln Thr His
1               5                   10                  15

Phe His Phe Glu Ser Pro Lys Leu Ile Ser Phe Lys Val Gln Asp Tyr
            20                  25                  30

Trp Ile Leu Asn Asp Ile Met Lys Lys Asn Leu Thr Gly Ile Ser Leu
        35                  40                  45

Lys Ser Glu Glu Glu Asp Ala Asp Ser Gly Glu Ile Asp
    50                  55                  60

<210> SEQ ID NO 6
<211> LENGTH: 20
<212> TYPE: PRT
<213> ORGANISM: Artificial sequence
<220> FEATURE:
<223> OTHER INFORMATION: synthetic

<400> SEQUENCE: 6

Glu Glu Gln Thr His Phe His Phe Glu Ser Pro Lys Leu Ile Cys Phe
1               5                   10                  15

Lys Val Gln Asp
            20

<210> SEQ ID NO 7
<211> LENGTH: 20
<212> TYPE: PRT
<213> ORGANISM: Artificial sequence
<220> FEATURE:
<223> OTHER INFORMATION: F2C

<400> SEQUENCE: 7

Phe Lys Val Gln Asp Tyr Trp Ile Leu Asn Asp Ile Met Lys Lys Asn
1               5                   10                  15

Leu Thr Gly Ile
            20

<210> SEQ ID NO 8
<211> LENGTH: 20
<212> TYPE: PRT
<213> ORGANISM: Artificial sequence
<220> FEATURE:
<223> OTHER INFORMATION: synthetic

<400> SEQUENCE: 8

Asn Leu Thr Gly Ile Ser Leu Lys Ser Glu Glu Glu Asp Ala Asp Ser
1               5                   10                  15

Gly Glu Ile Asp
            20

COMPOUND, USE, PHARMACEUTICAL COMPOSITION, METHOD OF DIAGNOSIS, METHOD OF TREATMENT, AND METHOD OF TRANSPORTATION AND/OR INTERNALIZATION OF A COMPOUND INTO EUKARYOTIC CELLS

FIELD OF THE INVENTION

The invention belongs to the technical fields of Pharmaceutical Sciences, Immunology, Diagnosis and/or Treatment for Cancer. Specifically, the invention relates to compounds for targeting molecular entities to the intracellular domain of eukaryotic/neoplastic cells, their use to modify other pharmaceutically active ingredients, a pharmaceutical composition comprising said compound and a method for diagnosis, prognosis and/or treatment of cancer or other cell-altering conditions.

DESCRIPTION OF THE STATE OF THE ART

Targeting active pharmaceutical ingredients (API) to tumor cells is a highly desirable feature for combating cancer and related cellular abnormalities. Even more desirable is targeting APIs selectively on tumor cells.

Cell penetration peptides (CPP) are well known in the art. In general, CPPs typically do not exceed 30 residues in length and generally carry a positive charge, which facilitates electrostatic interactions with the negatively charged cell surface. The compound of the invention it is also from peptide nature but it does not have the conventional characteristics of CPPs: its origin, sequence, chemical charge, type of bond and general physicochemical properties are very different.

The compound of the invention derives from the study of Amblyomin-X, which is a homologue of the Kunitz-type protein, identified in the transcriptome of the salivary glands of the adult tick *Amblyomma sculptum*, which was studied by the present inventors. The recombinant protein form of Amblyomin-X showed antitumor activity via apoptosis induction and proteasome inhibition. In addition, this molecule showed pro-apoptotic effects on tumor cells[1-3] and decreased tumor growth and in vivo metastasis[2,3]. The mechanism of action of Amblyomin-X involves inhibition of the proteasome, which occurs preferentially through the trypsin-like (T-L) activity of the proteasome[2]. Some of the present inventors have shown that, although the primary target of Amblyomin-X appears to be the proteasome, this macromolecule also inhibits autophagy through a suggested mechanism involving the activation of mTOR, which is transported by cytoplasmic dynein[4]. Furthermore, some of the inventors reported the pro-apoptotic effect of Amblyomin-X on these human tumor cells associated with inhibition of proteasome function, ER stress (increased expression of UPR markers), mobilization of $[Ca^{2+}]$, mitochondrial dysfunction, PARP cleavage and caspase activation[3]. Interestingly, none of these changes were observed in normal human fibroblast cells[5].

Despite years of intense study of Amblyomin-X by the inventors, they so far do not know of any previous reports describing or suggesting the compound of the invention, let alone its surprising and relevant technical effects. The closest scientific papers are recited below.

1. Akagi E M, Junior P L, Simons S M, Bellini M H, Barreto S A, Chudzinski-Tavassi A M. Pro-apoptotic effects of Amblyomin-X in murine renal cell carcinoma "in vitro". Biomedicine & pharmacotherapy=Biomedecine & pharmacotherapie 2012; 66: 64-9.
2. Chudzinski-Tavassi A M, De-Sa-Junior P L, Simons S M, Maria D A, de Souza Ventura J, Batista I F, et al. A new tick Kunitz type inhibitor, Amblyomin-X, induces tumor cell death by modulating genes related to the cell cycle and targeting the ubiquitin-proteasome system. Toxicon: official journal of the International Society on Toxinology 2010; 56: 1145-54.
3. Ventura J S, Faria F, Batista I F, Simons S M, Oliveira D G, Morais K L, et al. A Kunitz-type FXa inhibitor affects tumor progression, hypercoagulable state and triggers apoptosis. Biomedicine & pharmacotherapy=Biomedecine & pharmacotherapie 2013; 67: 192-6.
4. Pacheco M T, Berra C M, Morais K L, Sciani J M, Branco V G, Bosch R V, et al. Dynein function and protein clearance changes in tumor cells induced by a Kunitz-type molecule, Amblyomin-X. PloS one 2014; 9: e111907.
5. Morais K L, Pacheco M T, Berra C M, Bosch R V, Sciani J M, Chammas R, et al. Amblyomin-X induces ER stress, mitochondrial dysfunction, and caspase activation in human melanoma and pancreatic tumor cell. Molecular and cellular biochemistry 2016; 415: 119-31.
6. de Souza J G, Morais K L, Angles-Cano E, Boufleur P, de Mello E S, Maria D A, et al. Promising pharmacological profile of a Kunitz-type inhibitor in murine renal cell carcinoma model. Oncotarget 2016; 7: 62255-66.
7. Pacheco M T, Morais K L, Berra C M, Demasi M, Sciani J M, Branco V G, et al. Specific role of cytoplasmic dynein in the mechanism of action of an antitumor molecule, Amblyomin-X. Experimental cell research 2016; 340: 248-58.
8. Benavent Acero F R, Perera Negrin Y, Alonso D F, Perea S E, Gomez D E, Farina H G. Mechanisms of Cellular Uptake, Intracellular Transportation, and Degradation of CIGB-300, a Tat-Conjugated Peptide, in Tumor Cell Lines. Molecular pharmaceutics 2014; 11:1798-807.
9. Kristensen M, Birch D, Morck Nielsen H. Applications and Challenges for Use of Cell-Penetrating Peptides as Delivery Vectors for Peptide and Protein Cargos. International journal of molecular sciences 2016; 17.
10. Batista I F, Ramos O H, Ventura J S, Junqueira-de-Azevedo I L, Ho P L, Chudzinski-Tavassi A M. A new Factor Xa inhibitor from *Amblyomma cajennense* with a unique domain composition. Archives of biochemistry and biophysics 2010; 493:151-6.
11. Benedetti G, Morais K L, Guerreiro J R, de Oliveira E F, Hoshida M S, Oliveira L, et al. Bothrops jararaca peptide with anti-hypertensive action normalizes endothelium dysfunction involved in physiopathology of preeclampsia. PloS one 2011; 6: e23680.
12. Riedl S, Rinner B, Asslaber M, Schaider H, Walzer S, Novak A, et al. In search of a novel target-phosphatidylserine exposed by non-apoptotic tumor cells and metastases of malignancies with poor treatment efficacy. *Biochimica et biophysica acta* 2011; 1808: 2638-45.
13. Bohm G, Muhr R, Jaenicke R. Quantitative analysis of protein far UV circular dichroism spectra by neural networks. Protein engineering 1992; 5: 191-5.
14. Deleage G, Geourjon C. An interactive graphic program for calculating the secondary structure content of proteins from circular dichroism spectrum. Computer applications in the biosciences: CABIOS 1993; 9:197-9.
15—North American patent No.: U.S. Pat. No. 8,883,740 entitled Peptides, Compositions and Uses Thereof.

16—Canadian patent application CA2712807 entitled Peptides, Compositions and Uses Thereof.

17—Chudzinski-Tavassi A M, Carrijo-Carvalho L C, Waismam K, Farsky S H, Ramos O H, Reis C V. A lipocalin sequence signature modulates cell survival. FEBS Lett. 2010 Jul. 2; 584 (13): 2896-900.

18—Carrijo-Carvalho L C, Maria D A, Ventura J S, Morais K L, Melo R L, Rodrigues C J, Chudzinski-Tavassi A M. A lipocalin-derived Peptide modulating fibroblasts and extracellular matrix proteins. J Toxicol. 2012; 2012: 325250.

19—Jaffe E A, Nachman R L, Becker C G, Minick C R. Culture of human endothelial cells derived from umbilical veins. Identification by morphologic and immunologic criteria. J Clin Invest. 1973 November; 52 (11): 2745-56.

20—Alvarez Flores M P, Fritzen M, Reis C V, Chudzinski-Tavassi A M. Losac, a factor X activator from *Lonomia obliqua* bristle extract: its role in the pathophysiological mechanisms and cell survival. Biochem Biophys Res Commun. 2006 May 19; 343 (4): 1216-23.

21—Perea S E, Reyes O, Puchades Y, Mendoza O, Vispo N S, Torrens I, Santos A, Silva R, Acevedo B, Lopez E, Falcon V, Alonso D F. Antitumor effect of a novel proapoptotic peptide that impairs the phosphorylation by the protein kinase 2 (casein kinase 2). Cancer Res. 2004 Oct. 1; 64 (19): 7127-9.

To the best knowledge of the inventors, no state-of-the-art document reveals or even suggests the teachings of the present invention.

SUMMARY OF THE INVENTION

The present invention provides for compounds for targeting/internalizing molecular entities to the intracellular domain of neoplastic or cancerous eukaryotic cells. The invention also provides for the use of said compound to modify other active pharmaceutical ingredients so that said modified active ingredients are selectively targeted to eukaryotic, neoplastic or cancer cells. The invention also provides for a pharmaceutical composition comprising said compounds and a method for diagnosing, prognosing and/or treating cancer or other altered cell states.

The inventive concept underlying the objectives of the invention is a polypeptide compound having at least 80% identity with the polypeptide of SEQ ID No. 1, SEQ ID No. 6 or SEQ ID No. 7. Embodiments of the compound of the invention include: a polypeptide of SEQ ID No. 1, SEQ ID No. 6 or SEQ ID No. 7; fragments thereof; and/or cyclic modified forms thereof, including those modified with amide, alkyl-, alkoxy, halogen, hydroxy- or PEG groups, as well as those modified with other functional groups or amino acid/peptides, including unnatural amino acids such as d-forms of amino acids, salts of any of the above entities; and/or combinations thereof.

In one embodiment, the compound of the invention is used to modify small molecules, so that the resulting complex is enabled with the ability to penetrate into tumor cells.

In another embodiment, the compound of the invention is used to modify other peptide molecules, so that the resulting complex is enabled with the ability to penetrate into tumor cells.

These and other objects of the invention will be more readily appreciated by those skilled in the art by the evidence supporting the detailed description of the invention, as well as by the enclosed claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 11 schematically shows the compound of the invention (C-ter) chemically linked to a peptide known as P15 (Seq ID No 5).

FIG. 13 shows a schematic of Amblyomin-X sequence. The upper panel shows the entire sequence of Amblyomin-X sequence and delimitation of the Kunitz domain and carboxy-terminal end. In the lower panel, it shows the specification of each sequence derived from the carboxy-terminal end for synthesis of synthetic peptides with or without label.

DETAILED DESCRIPTION OF THE INVENTION AND SOME EMBODIMENTS

Figure 1:
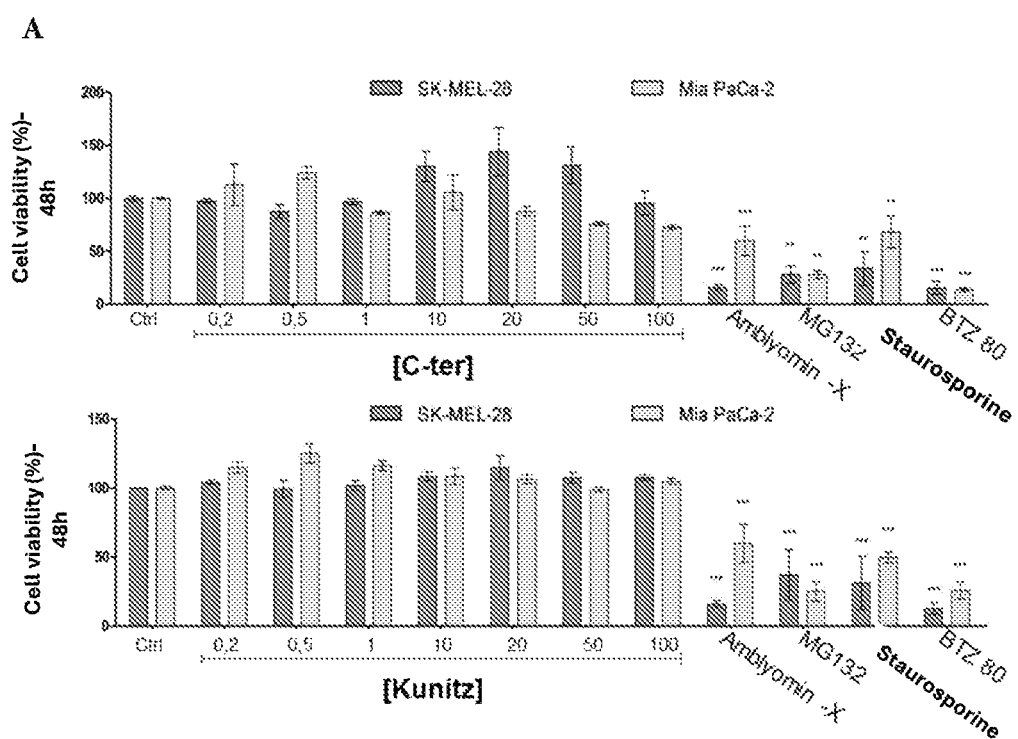
FIG. 1 reveals the non-cytotoxicity induced by an embodiment of the compound of the invention (denominated C-ter), and as a reference only to the Kunitz domain. After 48 h, cell viability of tumor cells (SK-MEL-28 and MIA PaCa-2) was measured by MTT using increasing concentrations (micromolar) of C-ter and Kunitz. Positive controls: 20 µM of entire Amblyomin-X, 5 µM of staurosporine, 80 nM of bortezomib (BTZ80) and 5 µM of MG132.

The present invention provides a compound for targeting molecular entities to the intracellular domain of neoplastic/cancer cells. The compound of the invention is peptide and has at least 80% identity with the polypeptide of SEQ ID No. 1, SEQ ID No. 6 or SEQ ID No. 7. Embodiments of the compound of the invention include: a peptide of SEQ ID No. 1, SEQ ID No. 6 or SEQ ID No. 7; a fragment thereof; and/or modified forms thereof, including modified cyclic, amide, alkyl-, alkoxy, halo, hydroxy- or PEG-forms, as well as forms modified with other functional groups or amino acids/peptides, including unnatural amino acids such as D-forms of amino acids, salts of any above entity; and/or combinations thereof.

In one embodiment the compound of the invention is a peptide and has at least 90% identity with the polypeptide of the SEQ ID No. 1, SEQ ID No. 6 or SEQ ID No. 7.

In one embodiment the compound of the invention is a peptide and has at least 95% identity with the polypeptide of the SEQ ID No. 1, SEQ ID No. 6 or SEQ ID No. 7.

The compound of the invention is synthetic. Such compound is useful for the preparation of a product of pharmaceutical interest selected from diagnostics, prognostics and/or therapeutic use in vertebrates, preferably a mammal.

The invention also provides for the use of said compound to modify other active pharmaceutical ingredients, so that said active ingredients are selectively targeted to neoplastic/cancer cells. The invention also provides for a pharmaceutical composition comprising said compound and a method for diagnosing, prognosing and/or treating cancer or other altered cell states.

In one embodiment, the compound of the invention is used to modify small molecules so that the resulting complex is enabled with tumor cell penetration capability. In another embodiment, the compound of the invention is used to modify other peptide molecules so that the resulting complex is capable of penetrating tumor cells. Detailed examples incorporated in the present invention include the modification of two different chemical entities as shown in table 1 below.

TABLE 1

Incorporation, by tumor cells, of two different chemical entities modified with the compound of the invention.

| Chemical entity 1 | Chemical entity 2 |
|---|---|
| 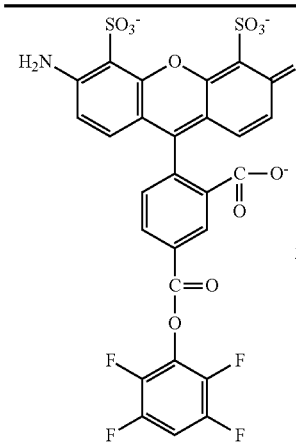 | Sequence peptide: YAIGYSSKDYK (Seq ID No. 2) |

Both chemical entities shown in the table above have little or no cell penetration capability, but when attached to the compound of the invention they have cell penetration capability. Furthermore, said chemical entities, when linked to the compound of the invention, also have the capacity for selective penetration of tumor cells.

For the purposes of the present invention the following definitions are used:

Product of Pharmaceutical Interest

In the context of the present patent application, "compound of pharmaceutical interest" shall be understood as any molecular entity that comprises the compound described as an inventive concept common to this patent application, also including molecular entities obtained through chemical modification/derivatization of the same, with the inclusion of other functional groups, linear or branched side chains, alteration of hydrophilicity or hydrophobicity, among others, provided that they comprise SEQ ID No. 1 or a fragment thereof as a core as defined above, excluding natural and already known entities.

Pharmaceutical Composition

In the context of the present patent application, "pharmaceutical composition" should be understood as any composition that contains an active ingredient, with prophylactic, palliative and/or curative purposes, acting in order to maintain and/or restore the homeostasis, which can be administered orally, topically, parenterally, enteral and/or intrathecally.

Pharmaceutically Acceptable Formulation

In the context of the present patent application, "pharmaceutically acceptable formulation" shall be understood as a formulation containing pharmaceutically acceptable excipients and carriers well known to persons skilled in the art, as is the development of convenient doses and treatments for use in particular compositions that can be described in a range of treatment regimens, including oral, parenteral, intravenous, intranasal, intravitreal and intramuscular, intracerebral, intracerebroventricular and intraocular and their administration and/or formulation.

Modified Peptide

In the context of the present patent application, "modified peptide" should be understood as an unnatural, artificially modified or synthesized peptide, including halides, cyclized, amidated, alkylated, alkoxylated, hydroxylated, PEGylated, other functional groups on any amino acid, or its salt forms, as well as with an amino acid or peptide, including unnatural ones such as d-amino acid forms. The peptide compound can be pegylated using techniques known to those skilled in the art, such as PEGylation with reagents containing the succinimidyl group, which preferentially react with primary amines present in the N-terminal region of the peptide. The peptide compound of the invention can be alkylated at any amino acid using techniques known to those of skill in the art, including, for example, the Mitsunobu reaction described in the article from Reichwein & Liskamp (Reichwein J F & Liskamp R M J. Site-specific N-alkylation of peptides on the solid phase. Tetrahedron Letters, Volume 39, Issue 10, 5 Mar. 1998, Pages 1243-1246). Said article describes the introduction of any alkyl group in a specific amide function of a peptide. The peptide compound of the invention may be alkoxylated, substituted with halogens, hydroxy or other functional groups on any amino acid using techniques known to those skilled in the art, including, for example, those described in the book/publication Special Periodic Reports, Amino Acids, Peptides and Proteins: Volume 42, Royal Society of Chemistry, 2013. The peptide compound of the invention can be modified with other molecular species useful in diagnostic and/or therapeutic applications, such as Biotin, using techniques known to those skilled in the art.

Cyclic or Circular Peptide

In the context of the present patent application, "cyclic, cyclized or circular peptide" is to be understood as a peptide that has had a covalent bond between the two ends of a linear peptide molecule by any method known in the art, particularly by enzyme activity. The cyclic peptide can be used in substitution of the linear peptide due to the fact that it is more difficult to be degraded, since its ends or attack zones by hydrolyzing enzymes are not as exposed as in a linear peptide.

In the context of the present patent application, the term "small molecule" should be understood as meaning conventional non-peptide/biological pharmaceutical entities, both for diagnostic and therapeutic use.

Example 1—Process for Obtaining the Compound of the Invention

In this embodiment, the compound of the invention is the polypeptide of SEQ ID No. 1 (C-ter) and was prepared by chemical synthesis by CEA. The compound was solubilized in $H_2O$.

Example 2—Use of the Compound of the Invention for Charge Delivery in Different Cell Types Cell Lines and Culture Conditions Human melanomas (SK-MEL-28), pancreatic adenocarcinomas (MIA-PaCa-2) and murine renal adenocarcinoma cells (RENCA) were obtained and cultured according to the instructions of the American Type Culture Collection (ATCC, Manassas, VA). Human dermal fibroblast cells (HDFa) were obtained from Invitrogen. Endothelial cells were obtained from human umbilical veins (HUVECs), as previously described[11]. The study received prior approval from the Research Ethics Committee and the free and informed consent form was obtained from female donors. HUVECs were seeded in T75 flasks previously covered with 2% gelatin and cultured in RPMI medium, supplemented with 10% fetal bovine serum, L-glutamine (2 mM), streptomycin sulfate (100 mg/ml), penicillin (100 U/ml) sodium pyruvate (100 mM), 2-mercaptoethanol (10 mM), ECGF (10 mg/ml) and heparin (45 µg/ml), pH 7.4. In all experiments, HUVEC were used in the second or third passages. All cell lines were routinely cultured in a humidified 5% $CO_2$ incubator at 37° C.

Cell Viability Assay

Cell viability was measured by the 3-(4,5-dimethylthiazol-2-yl)-2,5-diphenyltetrazolium bromide (MTT) assay. Briefly, after 48 hours of treatment with indicated concentrations of each compound, 20 µl of 5 mg/ml MTT was added to the cells and the plates were incubated for 3 h at 37° C. Afterwards, the medium was discarded, the dark blue crystalline formazan product was dissolved in 100 mL of dimethyl sulfoxide (DMSO), and the absorbance was measured in a Spectra MAX 190 microplate reader (Molecular Devices, Sunnyvale, USA) at 540 nm.

Cell Uptake Studies

The compound of the invention (C-ter) was chemically coupled with the amine reactive dye (Alexa fluor 488 tetra fluorophenyl acid tetra fluorophenyl ester (TFP)) using the Microscale Alexa Fluor® 488 Protein Labeling kit (Molecular Probes), following the manufacturer's instructions. Other entities (Amblyomin-X and its fragment called Kunitz domain) were also modified as described above, for comparative analysis.

To investigate the role of PS in C-ter uptake, cells were pretreated with Annexin V (5 μg/mL) or $Na_3VO_4$ (25 μM) and then incubated with fluorochrome-conjugated molecules for 4 hours.

The dye-conjugated protein was named 488-Amblyomin-X. Briefly, cells (104 cells/well) were seeded into 96-well plates. Once stabilized, the culture medium was replaced and cells were incubated with 488-Amblyomin-X (20 μM) at 37° C. for 2 h, 4 h and 24 h. The cells were then incubated with Alexa Fluor 555 transferrin (100 μg/ml), the cholera toxin B subunit Alexa Fluor 555 (50 μg/ml) or Alexa Fluor 555 dextran (1 mg/ml) in binding medium to 37° C. for 20 min. Nuclei were stained with Hoechst 332. Then, green and red fluorescence were monitored using a Molecular Devices ImageXpress Micro Confocal plate scanning microscope (Molecular Devices, Sunnyvale, CA) or using LSM 510 Meta confocal microscope (Zeiss, Jena, Germany) followed by evaluation of overlap between 488-Amblyomin-X and endocytosis markers using MetaXpress software (Molecular Devices, Sunnyvale, CA).

Microinjection Assay

SK-MEL-28 cells were plated on Cellocate glass coverslips for 24 h prior to injection. The microinjection solution was prepared with: 20 μM Amblyomin-X-488 or 10 μM Kunitz-647. Staurosporine (10 μM) was added directly to the medium for 6 hours and was used as a control for PI staining. Control cells were maintained in culture medium. The solution was injected into the cytoplasm of the cells (compensation pressure: 30 hPa; injection pressure: 100 hPa; injection time: 0.3 s). Immediately after injection, cells were replaced with fresh medium in an incubator at 37° C. After 4 h, cells were stained with PI (1 μg/mL—contain 100 ng/mL RNAse A) for 15 min at room temperature. Then, cells were washed twice with 1×PBS and fixed with 4% paraformaldehyde for 15 minutes at room temperature. Finally, the cells were washed with 1×PBS and a drop of Vectashield® anti-fade mounting solution (Vecta Labs) was applied to the plate with the coverslip containing the cells facing down and then sealed. The analysis was performed using a LSMS Zeiss 510 confocal microscope (Zeiss, Germany).

Intracellular Traffic by Indirect Immunofluorescence.

Tumor cells were cultured in 96-well plates (104 cells/well) and treated with 488-Amblyomin-X (20 μM) to indicate times. Cells were washed twice with PHEM-glycine buffer (2 mM HEPES, 10 mM EGTA, 2 mM $MgCl_2$, 60 mM Pipes, 100 mM glycine, pH 6.9) and fixed with 4% paraformaldehyde for 3 h at room temperature. The washing step was repeated and then the cells were incubated with a cell permeabilizing solution (0.1% Tween in PHEM) for 5 minutes at room temperature. Samples were washed and incubated with 1% BSA blocking solution for 30 minutes at room temperature. Next, the primary antibody was incubated overnight at 4° C.: (i) caveolin-1 anti-human mouse 1:100 (Santa Cruz Biotechnology, Inc., USA); (ii) 1:50 anti-human LAMP-2 rabbit (Abcam). A washing procedure was performed, and the samples were incubated with goat secondary antibodies Alexa Fluor® 555 anti-rabbit from (Invitrogen™ Life Technologies Inc., USA) and rabbit secondary antibodies Alexa Fluor® 647 anti-mouse (Invitrogen™ Life Technologies Inc., USA), both at 1:200 dilution for 1 h at room temperature in the dark. Hoechst 332 stained nucleus. Next, green and red fluorescence were monitored by a Molecular Devices ImageXpress Micro Confocal Plate Scanning Microscope (Molecular Devices, Sunnyvale, CA) followed by evaluation of overlap between 488-Amblyomin-X and endocytosis markers using MetaXpress software (Molecular Devices, Sunnyvale, CA) or vesicle interactions by Imaris software.

Detection of Membrane Containing OS

To measure endogenous PS exposure in the outer membrane leaflet, cultured cells were harvested, washed with phosphate buffered saline (PBS) and resuspended in 1× Annexin binding buffer (Invitrogen™, Life Technologies Inc.) containing 2.5 of FITC-Annexin V, followed by incubation for min in the dark at room temperature. Analysis was performed by FACS-Calibur or Aria flow cytometer (Becton Dickinson, St. Louis, MO). Data were evaluated using FlowJo software (Tree Star, Inc, Ashland, OR).

In a second approach, similar to that described by Riedl et. al., 2011, cells ($1 \times 10^5$) were seeded in 35 mm dishes. Then the medium was removed and the same annexin binding protocol was applied, as mentioned above. Then, unfixed cells were washed twice in appropriate culture medium and immediately observed under LSM 510 Meta confocal microscope (Zeiss, Jena, Germany).

Circular Dichroism (CD)

CD spectra were recorded on a JASCO J-810 spectropolarimeter equipped with a thermoelectric sample temperature controller (Peltiersystem).

C-ter domain samples (20 μM) were diluted in phosphate buffered saline (PBS), pH 7.4, or water using a total volume of 550 μL. Milli-Q water and protein-free buffer were used to calibrate the equipment. Scans were collected from 190 to 260 nm at 21° C. using a 1.0 mm (200 μL) light length quartz cell (Helma). The data were corrected and adjusted to the input buffer and the average residual ellipticity of the molars was calculated based on the molecular mass of each compound. The estimation of the secondary structure was performed using the CDNN CD13 spectra deconvolution software and the DicroProt14 program.

Statistical Analysis

Comparisons were performed using Two-way ANOVA analysis followed by Tukey's Post Hoc test or t-Test, using the GraphPad Prism 5.0 software (GraphPad Software Inc., San Diego, CA). The criteria for statistical significance were established as * $P \leq 0.05$. $P \leq 0.01$ e *$P \leq 0.001$.

Chage Delivery Capacity of the Compound of the Invention

Endothelial cell culture was obtained from umbilical cords by digestion of umbilical cord veins with collagenase as described previously (19) with some modifications (20). Endothelial cells between the first and third passage were used for all experiments. Cells were seeded in 96-well culture plates (Advance, Greiner), special for immunofluorescence, at a density of $8 \times 10^3$ cells/well pre-coated with 2% (w/v) gelatin in EGM®-2 BulletKit® medium for HUVECs (Lonza, CC-3162) allowed to seed at 37° C. in a humidified atmosphere of 5% $CO_2$. Cells were treated and incubated in RPMI medium containing 1% fetal bovine serum (FBS) and Alexa-Fluor 488 labeled peptides (C-ter/Seq ID No 1, P4/Seq ID No 2, or P4-Cter/Seq ID No 3) at different concentrations and times. After treatment, the cells were fixed with 4% paraformaldehyde and analyzed in ImageXpress Micro Confocal High-Content Imaging (HCS, Molecular Devices) in Widefield mode and the number of vesicles containing the peptides in the cells was quantified using MetaXpress High-Content Image Acquisition and Analysis Software (Molecular Devices).

Example 3—Use of the Compound of the Invention in a Pharmaceutical Product

Effect of the Compound of the Invention (Cter) on Tumor and Non-Tumor Cells

The effect of the compound of the invention alone was investigated on the viability of human tumor cells, including melanoma (SK-MEL-28) and pancreatic adenocarcinoma (Mia-PaCa-2) cells using MTT assays. After 48 hours no change was observed. In contrast, Amblyomin-X and positive controls decreased the cell viability of both tumor cells (FIG. 1A).

Figure 2:
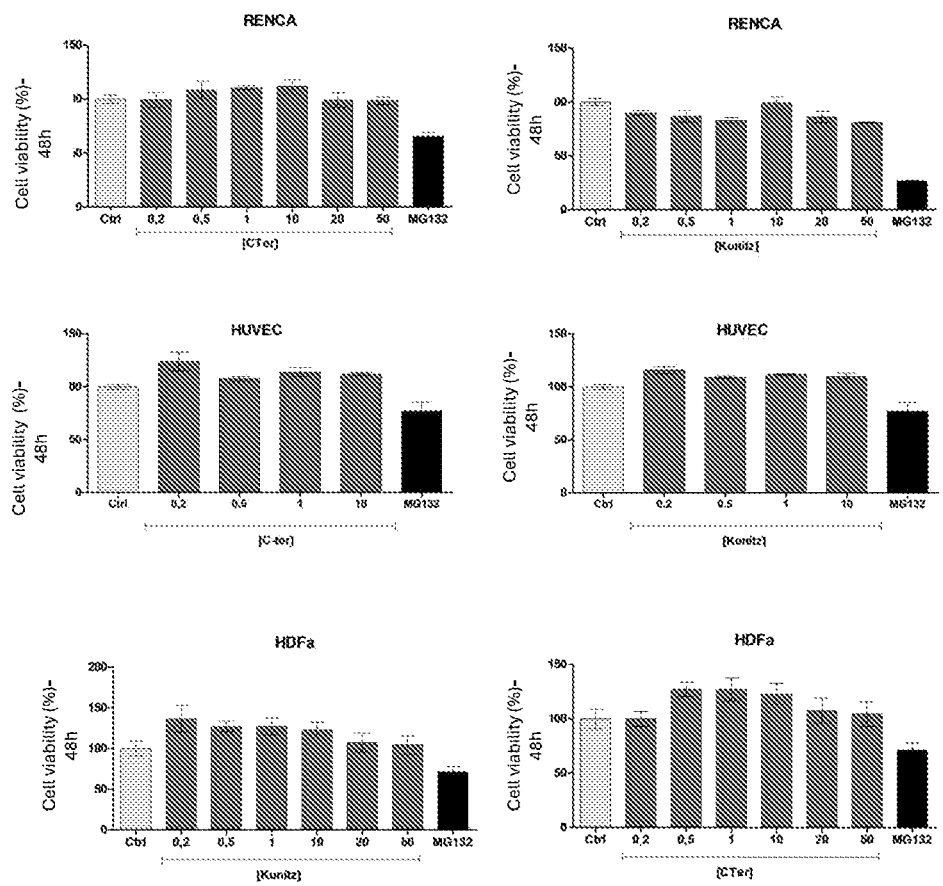
FIG. 2 shows the effects of one embodiment of the compound of the invention (C-ter) on cell viability of tumor and non-tumor cells compared to the Kunitz domain of Amblyomin-X. Cells were incubated with increasing concentrations of C-ter or Kunitz for 48 h at 37° C. MG-132 (5), a known proteasome inhibitor, was used for 48 h, as a positive control. Then, cell viability was measured by the reduction of MTT.

In addition, preliminary results were obtained with murine renal adenocarcinoma cells (RENCA), human dermal fibroblasts (HDFa) and human umbilical vein endothelial cells (HUVEC). Except for decreasing the viability of RENCA by 1 µM, again no change was observed (FIG. 2).

Only the C-Ter Domain is Taken Up by Tumor and Non-Tumor Cells

The Cter domain was complexed with the cell-impermeable Alexa Fluor 488. After 4 hours, it was observed that the Cter domain (20) was taken up by SK-MEL-28 (tumor cells). However, Kunitz (20 µM for 4 h) was not detected inside the cells (FIG. 3A), suggesting that C-ter is responsible for the uptake of Amblyomin-X. Furthermore, after complete Kunitz or Amblyomin-X microinjection (both 20 µM), propidium iodide (PI) staining was detected in SK-MEL-28 (FIG. 3B), suggesting a decrease in cell viability. Microinjection cells were not used as a control. This result indicates that the Kunitz domain may be responsible for cytotoxicity and its internalization is crucial for this effect.

In addition, we quantified the uptake of C-ter and Amblyomin-X and observed that the accumulation of C-ter within cells is faster than Amblyomin-X (Table 2), and few cells were positive for nuclear translocation (FIG. 3C).

TABLE 2

Uptake of C-ter and Amblyomin-X by tumor cells

| Cell type | Time (h) | C-Ter | Amblyomin-X |
|---|---|---|---|
| SK-MEL-28 | 0.25 | 30.84 ± 17.2 | 15.13 ± 2.71 |
|  | 0.5 | 35.56 ± 21.09 | 29.89 ± 12.27 |
|  | 1 | 62.17 ± 11.20 | 35.23 ± 17.32 |
|  | 2 | 558.48 ± 189.00 | 139.57 ± 71.44 |
|  | 4 | 1210.74 ± 379.14 | 988.76 ± 409.20 |
| Mia PaCa-2 | 0.25 | 3.45 ± 1.34 | 0.38 ± 0.25 |
|  | 0.5 | 4.84 ± 1.95 | 2.77 ± 1.96 |
|  | 1 | 13.74 ± 7.15 | 7.422 ± 0.81 |
|  | 2 | 604.99 ± 24.47 | 76.69 ± 20.72 |
|  | 4 | 976.55 ± 74.55 | 1001.40 ± 317.54 |

Figure 4:
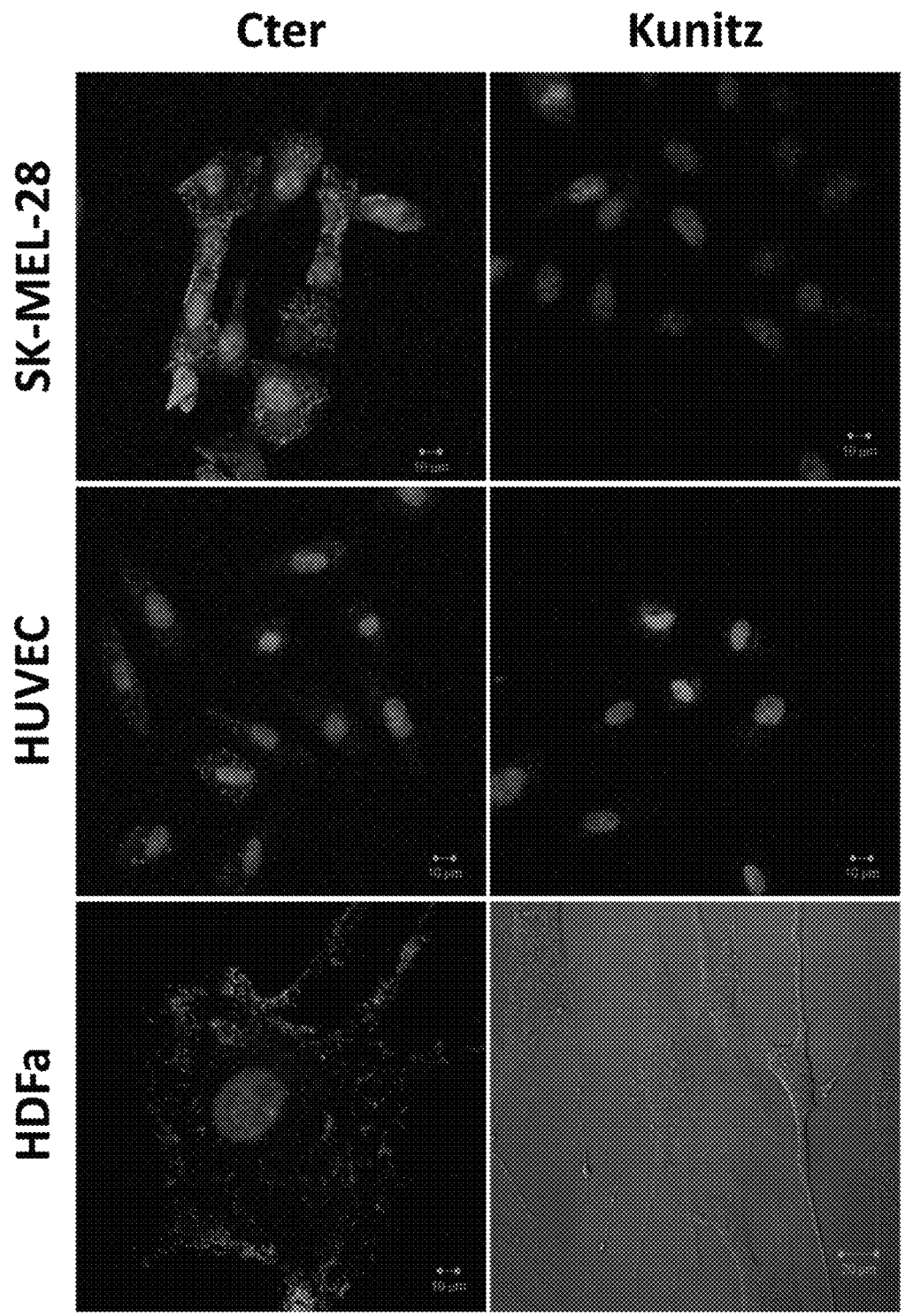
FIG. 4 shows that the compound of the invention is taken up by the tumor and, to a lesser extent, by non-tumor cells (HUVEC, HDFa cells). Cells were incubated with Amblyomin-X-488 (1 µM), Cter-488 (10 µM), Kunitz-488 (10 µM) or Alexa Fluor 488 (0.5 nM) for 4 h. Green fluorescence was monitored with confocal laser scanning microscopy.

Similar results were obtained with HUVEC and HDFa in preliminary experiments (FIG. 4), i.e., C-ter uptake by these cells. We investigated whether higher concentrations of Kunitz (100 µM) would affect uptake studies and, after 4 hours of treatment, vesicles ten times smaller than Amblyomin-X were detected (Table 3).

TABLE 3

Kunitz absorption by tumor cells

| Cell type | Time (h) | Kunitz (10 µM) | Kunitz (100 µM) |
|---|---|---|---|
| SK-MEL-28 | 2 | 0.26 ± 0.024 | 4.14 ± 3.76 |
|  | 4 | 1.12 ± 0.11 | 37.64 ± 0.16 |
| Mia PaCa-2 | 2 | 0.8 ± 0.28 | 13 ± 5.93 |
|  | 4 | 1.86 ± 1.31 | 98 ± 49.73 |

Figure 5:
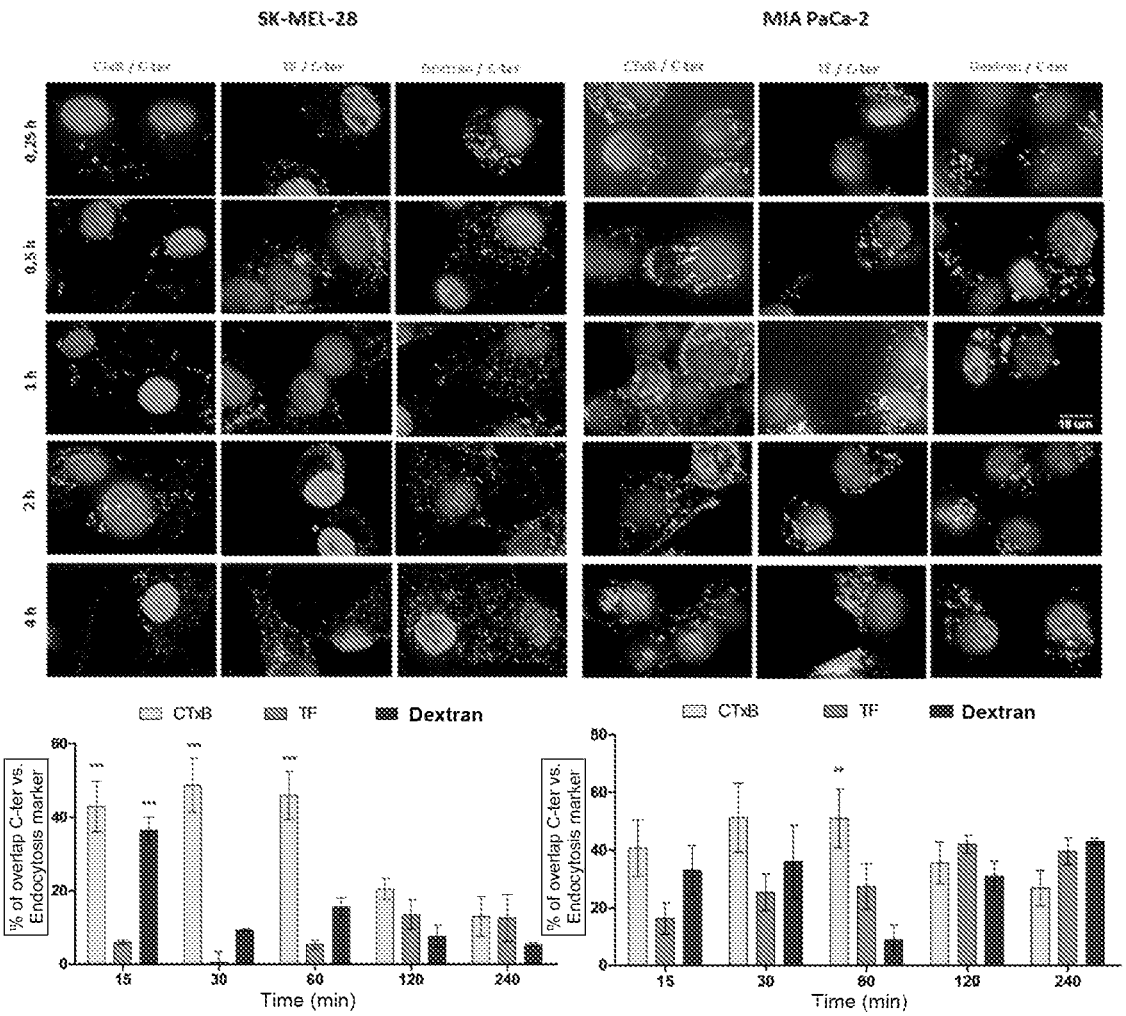
FIG. 5 shows the compound of the invention used to modify a pharmaceutical ingredient used for diagnostic purposes. The incorporation of C-ter-488 was initiated by lipid rafts. Tumor cell lines were treated with C-ter-488 at the indicated times; the cells were then incubated with Alexa Fluor 555 blot (100 mg/ml), the Alexa Fluor 555 cholera toxin B subunit (50 mg/ml) or the Alexa Fluor 555 dextran (1 mg/ml) in binding medium at 37° C. for 20 min. Then, green and red fluorescence was monitored using a Molecular Devices ImageXpress Micro Confocal plate scanning microscope. The nucleus was stained with Hoechst 332. The overlap between C-ter and endocytosis markers was analyzed using MetaXpress software (Molecular Devices, Sunnyvale, CA).

Incorporation of C-Ter by Lipid Rafts and Caveosomes and Lysosomes as Intracellular Destination We investigated the endosomal pathway used by C-ter through co-localization assay using Alexa Fluor 555 labeled dextran, cholera toxin B subunit (CTxB) or transferrin. As seen in FIG. 5, overlapping points were found between C-ter and all markers, but the highest were with CTxB, specifically at the shortest treatment time, suggesting that C-ter uptake occurs by caveolin-mediated endocytosis. Thus, co-localization with cav-1 (FIG. 6) occurred mainly after 4 hours of treatment. Furthermore, C-ter was found in co-localization with late endosomal markers, Lyso Tracker and LAMP-2, especially in MIA PaCa-2.

The compound of the invention retains its ability to penetrate tumor cells even after pretreatment with $Na_3VO_4$ or pretreatment with Annexin V (a PS ligand).

Figure 6:
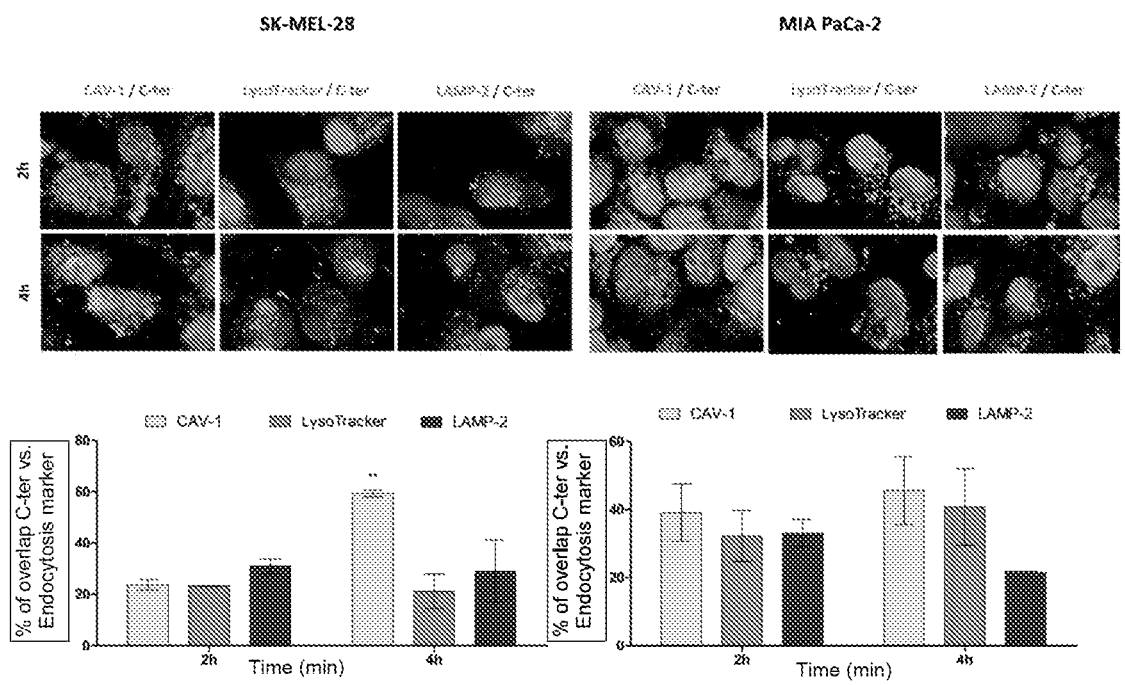
FIG. 6 shows that the compound of the invention and/or its charge is/are targeted to the caveosome and/or lysosomes as an intracellular destination. Tumor cell lines were treated with 488-Cter at the indicated concentration. Then, cells were incubated with a primary antibody against caveolin-1 or LAMP-2, followed by a secondary antibody conjugated to Alexa Fluor 555. In addition, after treatment, cells were incubated with Lyso Tracker Red DND 99 (100 nM) in medium binding at 37° C. for 20 min. Then, the green and red fluorescence were monitored using a Micro Devices plate scanning microscope from Molecular Devices ImageXpress. The nucleus was stained with Hoechst 332. The overlap between C-ter and intracellular markers was analyzed using MetaXpress software (Molecular Devices, Sunnyvale, CA).
Figure 7:
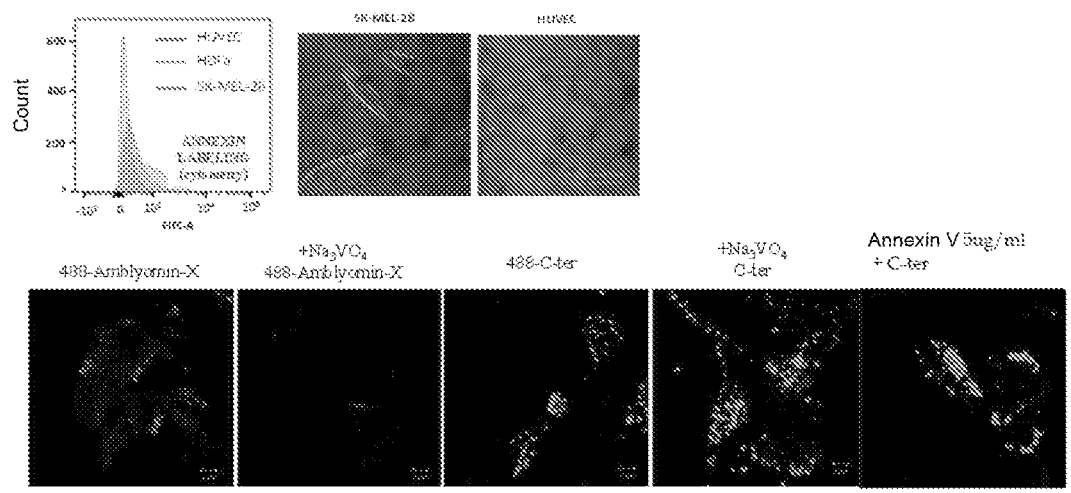
FIG. 7 shows selective uptake of Amblyomin-X via PS (phosphatidylserine) recognition. (A) The amount of PS exposed on the cells was analyzed by labeling with FITC-Annexin V, followed by FACS analysis or confocal microscopy. (B) SK-MEL-28 cells were pretreated with Na3VO4 (sodium orthovanadate—an inhibitor of PS synthesis) for 2 h. Then, cells were incubated with Amblyomin-X-488 (1), P1-488 (10) for 4 h. Green fluorescence was monitored with confocal laser scanning microscopy.

Tumor cells have more exposure to anionic phospholipids (phosphatidylserine—PS) on their cell surfaces. As seen in FIG. 6, tumor cell lines (SK-MEL-28) are more positive for Annexin-5 labeling, suggesting more exposure to PS compared to non-tumorigenic cells (HDFa and HUVEC), regardless of apoptosis activation. Furthermore, when human melanoma cells were pretreated with $Na_3VO_4$ (sodium orthovanadate—an inhibitor of PS synthesis), or, in other words, when PS exposure was decreased, C-ter uptake was not affected. by pre-treatment with $Na_3VO_4$. Annexin V (a PS ligand). Amblyomin-X, in contrast, was only slightly detected within these cells.

Example 4—Structural Analysis of the Compound of the Invention

C-Ter is a Random Structure Compound

Figure 8:
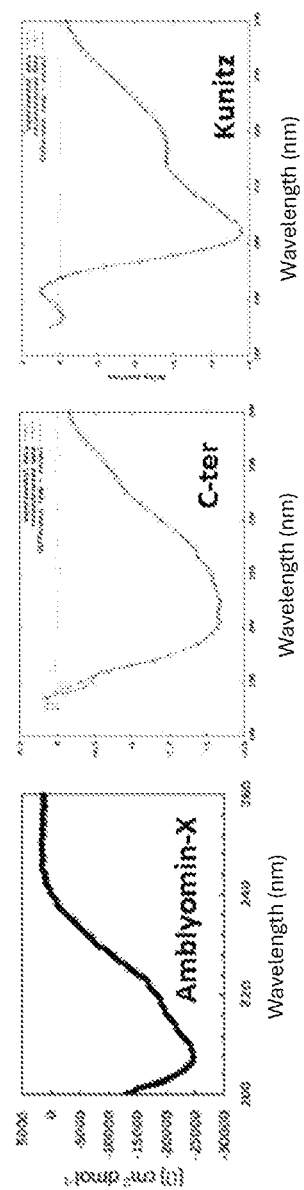
FIG. 8 shows the circular dichroism analysis of the C-ter compound of the invention and Kunitz for comparison. Spectra were measured at a peptide concentration of 20 µM. The result for Amblyomin-X is from Pasqualoto et. al., 2014—Protein & Peptide Letters.

The analysis of circular dichroism shows that the compound of the invention is mostly of random structure (FIG. 8).

Ability to Deliver Charge by Conjugation with a Cell Membrane Permeable Molecule To further demonstrate the ability of C-ter to be used as a chemical charge delivery entity, the compound of the invention (Seq ID No 1, 50 amino acids) was chemically linked to a peptide having 10 amino acids belonging to the well-known cytoprotective peptide (SEQ ID No. 2, sequence YAIGYSSKDYK-OH, called peptide P4, References 15-18), thus forming a hybrid peptide. P4 is known for its low penetration capacity. The hybrid peptide in this embodiment of the invention thus comprises 60 amino acids with the following sequence (SEQ ID No. 3):

YAIGYSSKDYKGGGGEEQTHFHFESPKLIS-FKVQDYWILNDIMKKNLT GISLKSEEEDADSGEID

Figure 3:
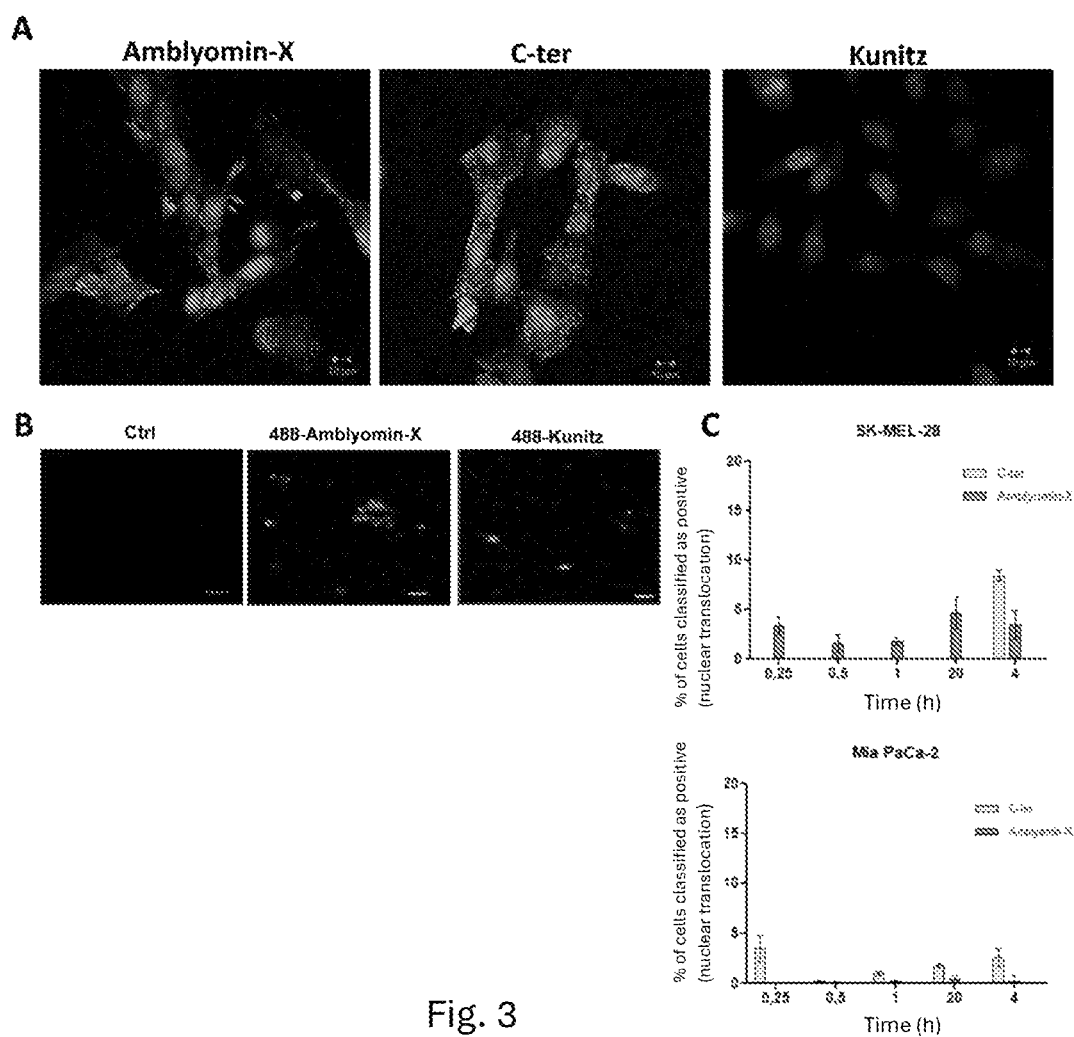
FIG. 3 shows the internalization of an embodiment of the compound of the invention per tumor. (A) Cells were incubated with C-ter-488 (20) and, for comparison, Kunitz-488 or Amblyomin-X-488 (20), during 4 h. Green fluorescence was monitored with confocal laser scanning microscopy. The nucleous was stained with 5 µM of Syto59. (B) Microinjection of Kunitz-488 and Amblyomin-X-488 triggers cell death in human melanoma cells. Cells were microinjected with 20 µM of Kunitz or Amblyomin-X and incubated for 4 h, when cell death was marked, based on green fluorescence and PI staining. (C) Percentage of cells positive for C-ter and Amblyomin-X nuclear translocation in SK-MEL-28 and MIA PaCa-2 cells. Both vesicles (C-ter and Amblyomin-X) or nuclear translocation were analyzed using MetaXpress software (Molecular Devices, CA).
Figure 9:
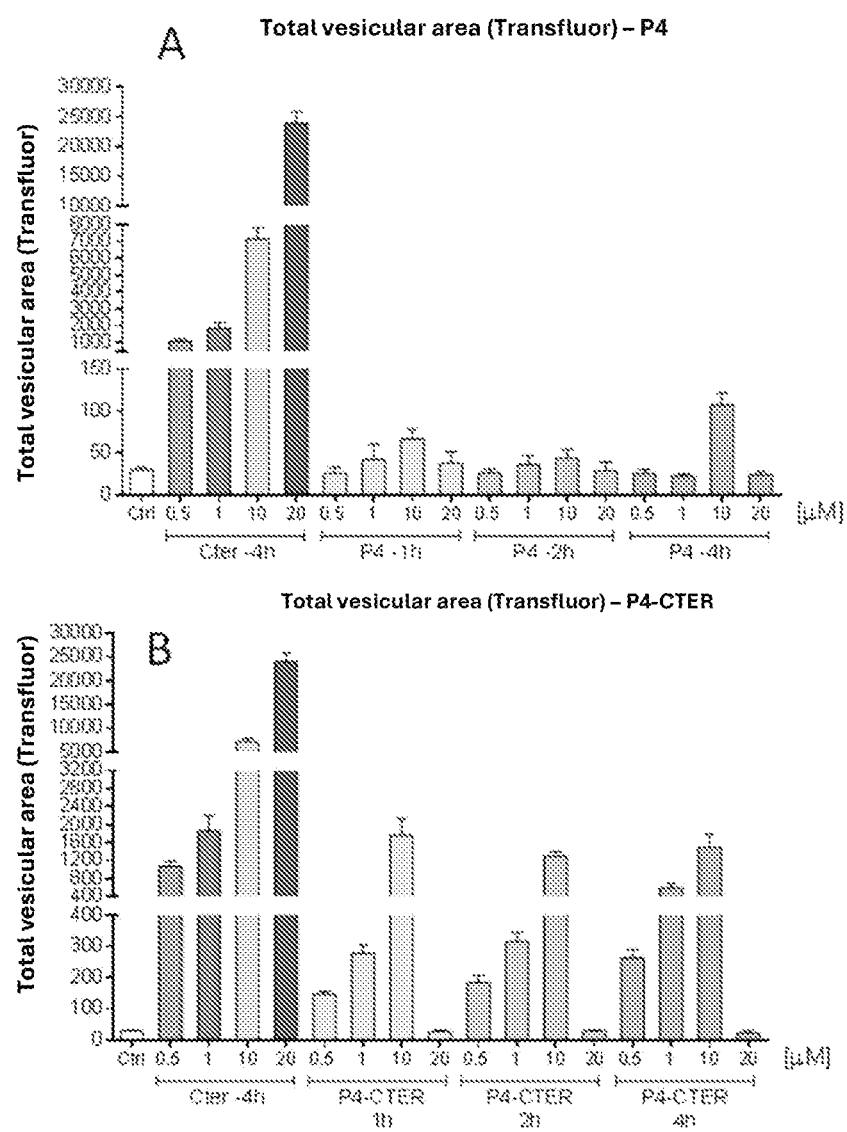
FIG. 9 shows the charge delivery capacity of the compound of the invention. C-ter-Alexa 488 was efficiently absorbed in HUVECs after 4 hours with 20 µM being the best uptake concentration. Peptide P4-Alexa 488 was poorly detected after 4 h at 10 µM, while said compound modified with the compound of the invention, that is, P4-Cter-Alexa488 was efficiently absorbed at a concentration of 10 µM already after 1 h. Green fluorescence was monitored by High Content Screening (HCS).
Figure 10:
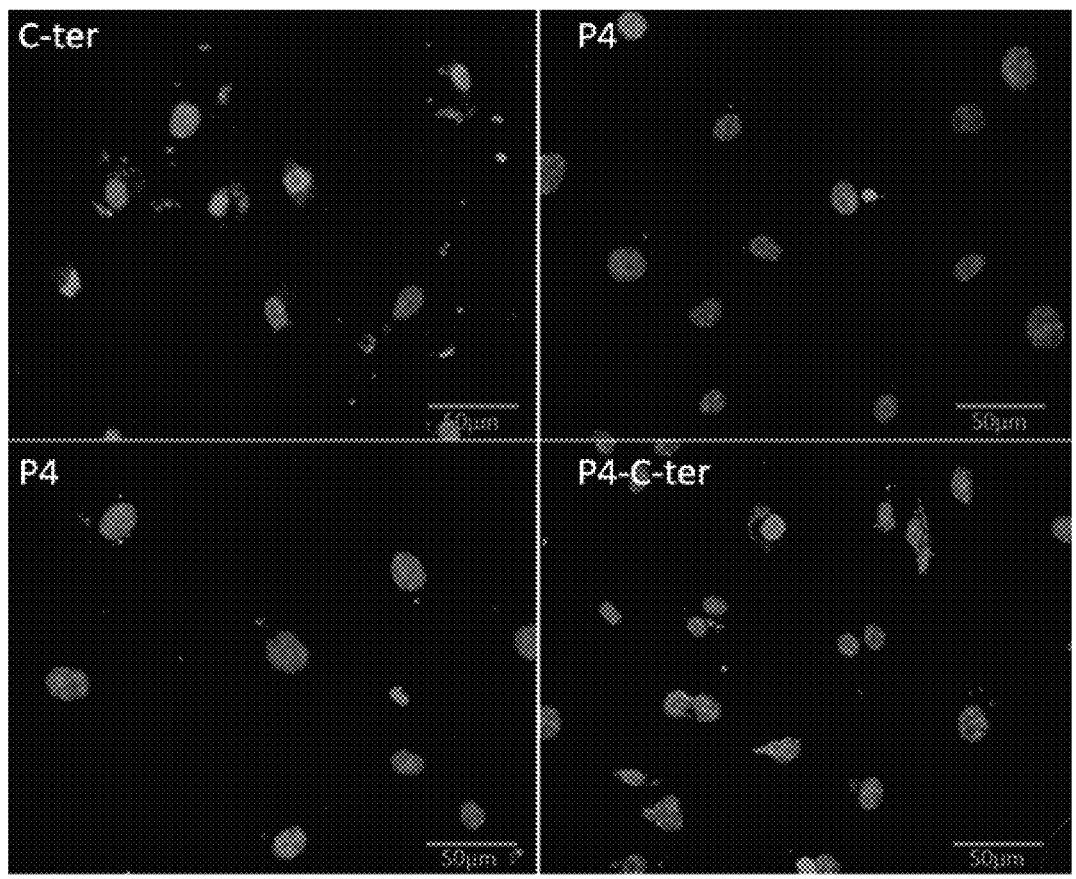
FIG. 10 shows that the compound of the invention, itself or chemically modified (Cter and P4-Cter), is absorbed by HUVECs. Representative HCS images for C-ter (4 h, 20 µM) and P4 (4 h, 10 µM) uptake. Green fluorescence was monitored by High Content Screening (HCS). CTRL Alexa 488 is an isolated Alexa Fluor 488 dye control.

Peptides Cter, P4 and P4-Cter were labeled with cell-impermeable Alexa Fluor 488. The capacity of P4 and P4-Cter peptides bound to Alexa 488 by HUVECs at 1 h, 2 h and 4 h was analyzed using different concentrations: 0.5 µM, 1 µM, 10 µM and 20 µM (FIG. 9). This was compared with uptake of C-ter peptide linked to Alexa 488 (concentration of 0.5 µM, 1 µM, 10 µM and 20 µM) after 4 hours, as shown in previous experiments for SK-MEL-28 (FIG. 3). The results demonstrated that P4-Alexa 488 was not detected within cells after 4 h (FIG. 9A and FIG. 10), in contrast to P4-C-ter-Alexa 488, which was captured and quantified (FIG. 9B and FIG. 10) within the cells. This result shows that C-ter provided the internalization of the P4 peptide into cells.

In view of the results presented above, it is possible to conclude that the compound of the invention has the ability to deliver charge within tumor cells, this charge being a peptide or a small molecular entity. Furthermore, when functions are compared, the C-terminal domain is responsible for the incorporation of Amblyomin-X by tumor cells, while the Kunitz-type domain of Amblyomin-X is associated with its cytotoxicity to tumor cells. Furthermore, the internalization of the C-terminal domain and intracellular traffic are similar to Amblyomin-X.

First, the C-ter charge delivery capacity indicates that this molecule is similar in function to a cell-penetrating peptide (CPP). However, C-ter does not have conventional characteristics of CPPs, as its origin, sequence, chemical charge, type of bond and general physicochemical properties are very different. In general, CPPs typically do not exceed 30 residues in length and generally carry a positive charge, which facilitates electrostatic interactions with the negatively charged cell surface. In contrast, C-ter has 50 residues and a negative formal charge[8, 9]. Furthermore, if an endocytic mechanism is elevated by a CPP for intracellular delivery of its charge, a successful result is related to the endosomal escape potential before being directed to the lysosomes for degradation or recycling of endosomes for transport back to the plasma membrane and subsequent extracellular release[9]. In this regard, the compound of the invention showed promising results. Even with colocalization in late endosome markers, it was found in the other subcellular structure (caveosomes).

Example 5—the Compound of the Invention Also Provides for the Internalization of the P15 Peptide In this embodiment, also a further hybrid peptide was synthesized in order to validate the ability of the compound of the invention (Cter) as a charge delivery peptide by conjugating the Cter sequence (50 amino acids) with a poorly permeable molecule to the cell membrane, namely P15 (Seq ID No. 4, 7128.99 Da, Perea et al., 2004). FIG. 11 schematically shows the compound of the invention chemically linked to a peptide known as P15, forming the complex of Seq ID No 5.

The compound of the invention (Cter, 5856 Da), the peptide P15 (1290.54 Da) and Cter-P15 (7128.99 Da) were labeled with Alexa Fluor 488 TFP dye (Life Technologies #A30006) according to the manufacturer's instructions.

To show the internalization capacity of the compound of the invention, SK-MEL-28 cells were seeded in a 96-well plate (Advanced, Greiner #655-986) at the density of $7 \times 10^3$ cells/well for 24 h in DMEM High Glucose, medium supplemented with 10% fetal bovine serum (FBS) and 1% penicillin/streptomycin (Sigma). The compounds Cter-Alexa 488, P15-Alexa 488 and Cter-P15-Alexa 488 at a concentration of 10 µM were added to the cells and incubated for 4 h. The cells were subjected to fixation steps for further analysis by High Content Screening (HCS). For this, cell monolayers were washed three times with PHEM buffer (2 mM HEPES, 10 mM EGTA, 2 mM $MgCl_2$, 60 mM PIPES—pH 6.9) and fixed for 1 h with cold 4% paraformaldehyde. Nuclei were stained with Hoechst (5 µM) for 5 min. The samples were submitted to high-content image analysis using ImageCpress Micro Confocal High-Content Imaging (HCS, Molecular Devices) in confocal mode and the number of vesicles containing the peptides in the cells was quantified using the MetaXpress High-Content Image Acquisition software & Analysis. (Molecular Devices).

Figure 12:
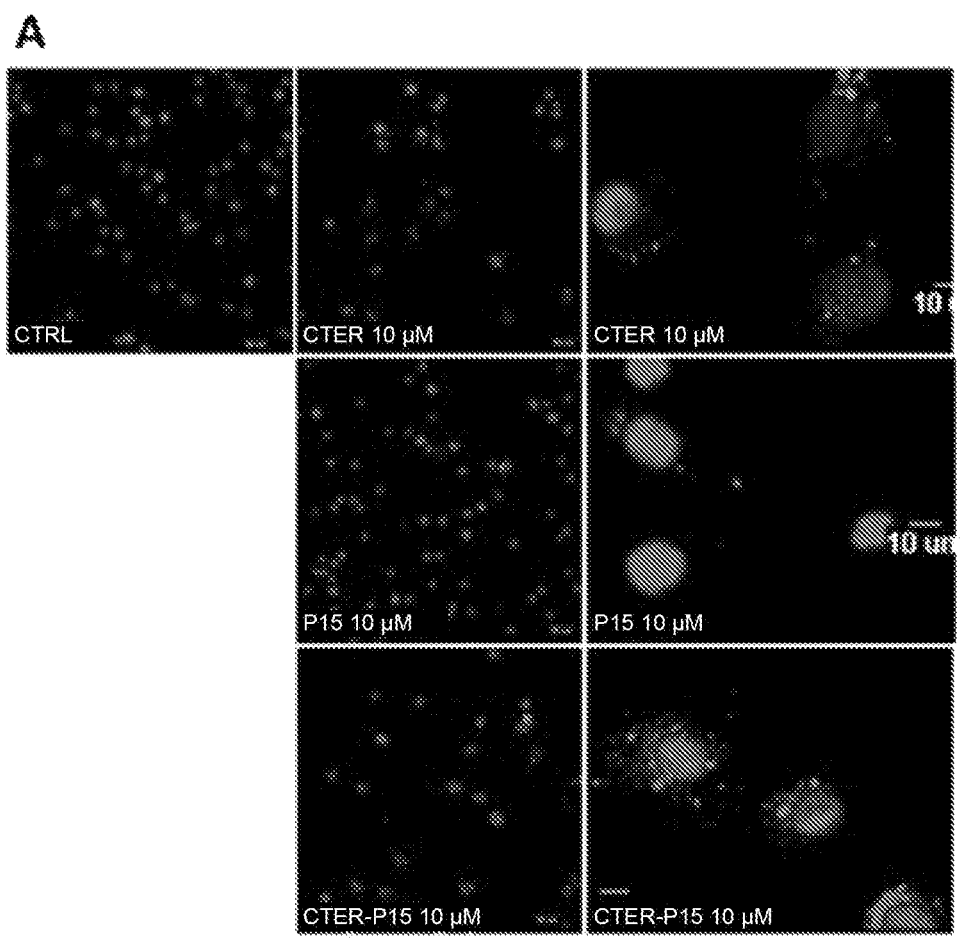
FIG. 12 shows that the compound of the invention provides for the uptake by HUVECs of yet another peptide known as P15. A) shows representative images of HCS for incorporation of Control (CTRL) C-ter (4 h, 10 µM), P15 (4 h, 10 µM) and C-ter-P15 (4 h, 10 µM); B) shows a graph with cell quantification: vesicle count (transfluor, 9 sites/well) of test compounds vs. control.
Figure 12:
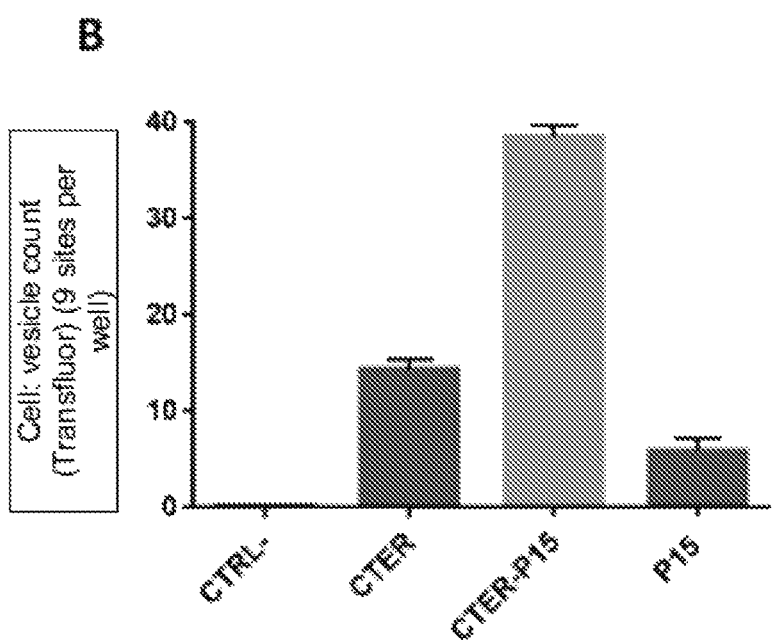

FIG. 12 shows the charged delivery capacity of the compound of the invention. A) Representative HCS images for capture of Cter-Alexa 488, P15-Alexa 488 and Cter-P15-Alexa 488. B) Quantification of the number of vesicles by green fluorescence by High Content Screening (HCS). The results show that Cter-Alexa 488 (10 µM) was efficiently absorbed into SK-MEL-28 after 4 h while peptide P15-Alexa 488 was poorly detected. The compound P-15 modified with the compound of the invention, i.e., Cter-P15-Alexa 488 was efficiently absorbed at a concentration of 10 µM after 4 h.

Example 6—Additional Fragments of the CTer Fraction of Amblyomin-X and their Internalization Three synthetic peptides derived from the carboxy-terminal end of Amblyomin-X were synthesized. These peptides were named: F1C (AA1-AA20) SEQ ID No. 6, F2C (AA16-AA35) SEQ ID No. 7 and F3C (AA35-AA50) SEQ ID No. 8, as well as the respective version tagged with fluorescein isothiocyanate-FITC (F1C-FITC, F2C-FITC, F3C-FITC). After standardization of concentration and quantification of the synthetic peptides tagged with the fluorophore, the internalization assays were started in SK-Mel-28 cells in short incubation times using HCS. For this, initially two concentrations of each probe (1 µM and 10 µM) were used to carry out incubations of 1 h and 6 h. Internalization of F1C-FITC and F2C-FITC was seen at both concentrations, in a dose-dependent manner. F3C-FITC did not show internalization even at the highest concentrations used. Images were analyzed by confocal microscopy and the internalization of F1C-FITC and F2C-FITC peptides was seen, showing a similar pattern of subcellular localization. The amount of F2C-FITC within SK-Mel-28 cells was higher compared to the amount of F1C-FITC, suggesting that F2C-FITC is more easily incorporated by the cells. This difference in fluorescence emission can be guaranteed by the close number of cells between treatments, which supports the best result of F2C-FITC. With this set of results, it can be suggested that the F2C fragment derived from the carboxy-terminal portion of Amblyomin-X may be involved in molecular internalization and could be considered a CPP.

Methodology. Approximately $1 \times 10^3$ SK-Mel-28 cells were seeded per well of 96-well plates (Greiner bio-one, Kremsmunster, Austria), which were maintained under the same conditions as described by Pacheco et al (2014). For the treatment with the different synthetic peptides labeled with fluorescein isothiocyanate (FITC) concentrations of 1, 5 and 10 µM were used. As a control, cells were treated with the FITC-labeled carboxy-terminal end (C-Ter-FITC). 1, 2, 4 and 6 h after treatment, cells were washed three times with warm 1×PBS and then fixed in 4% paraformaldehyde for 30 min. After the fixation time, the cells were incubated with a solution of DAPI (4',6-diamidino-2-phenylindole) in PHEM-Triton X-100 buffer for 15 min for nucleus marking. After marking the nucleus, the solution was removed and the cells washed three times with warm 1×PBS for fluorescence analysis.

Results. Three synthetic peptides derived from the carboxy-terminal end of Amblyomin-X were synthesized. These peptides were named: F1C (AA1-AA20), F2C (AA16-AA35) and F3C (AA35-AA50), as well as the respective version labeled with fluorescein isothiocyanate-FITC (F1C-FITC, F2C-FITC and F3C-FITC) (FIG. 13).

Figure 14:
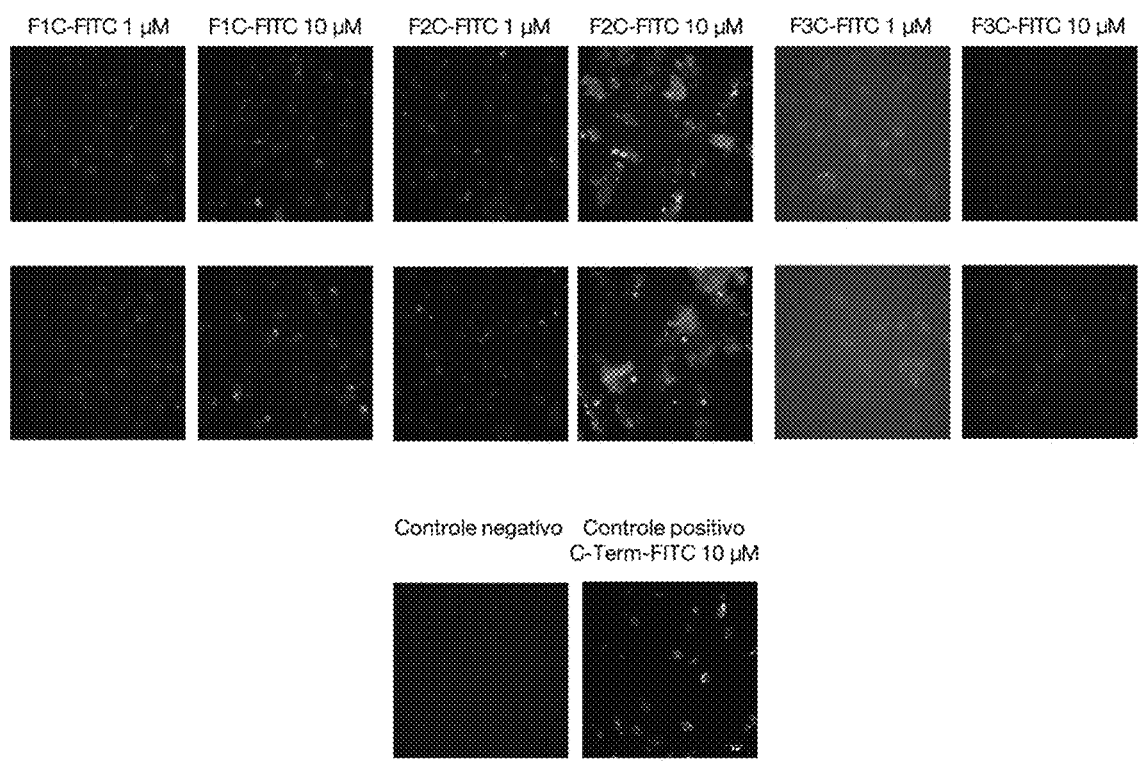
FIG. 14 shows the standardization of the concentration of the labeled synthetic peptides in SK-Mel-28 cells during 6 h of treatment by HCS. SK-Mel-28 cells were incubated with the different labeled synthetic peptides for 6 h and evaluated by HCS. The F1C-FITC and F2C-FITC peptides had higher fluorescence intensity at concentrations of 10 µM. The difference between the F3C-FITC peptide that did not fluoresce even at the highest concentration. In the lower panel, images of the negative (unmarked) and positive (full C-ter) controls. The nuclei were blue stained with DAPI (500 nM).

After standardization of concentration and quantification of synthetic peptides labeled with fluorophore, internalization assays in SK-Mel-28 cells in short times of incubation by means of HCS was started. For this, initially two concentrations of each probe (1 and 10 µM) were used to carry out incubations of 1 and 6 h (FIG. 14). Higher fluorescence intensity of F1C-FITC and F2C-FITC was seen at both concentrations and as expected, in a dependent manner. F3C-FITC did not show fluorescence even at the highest concentrations used (FIG. 14). As a positive control, the full end of the FITC-labeled carboxy-terminal (C-Term-FITC)

was used, already well known for its internalization capacity, but the used probe aliquot did not work as expected (FIG. 14).

Figure 15:
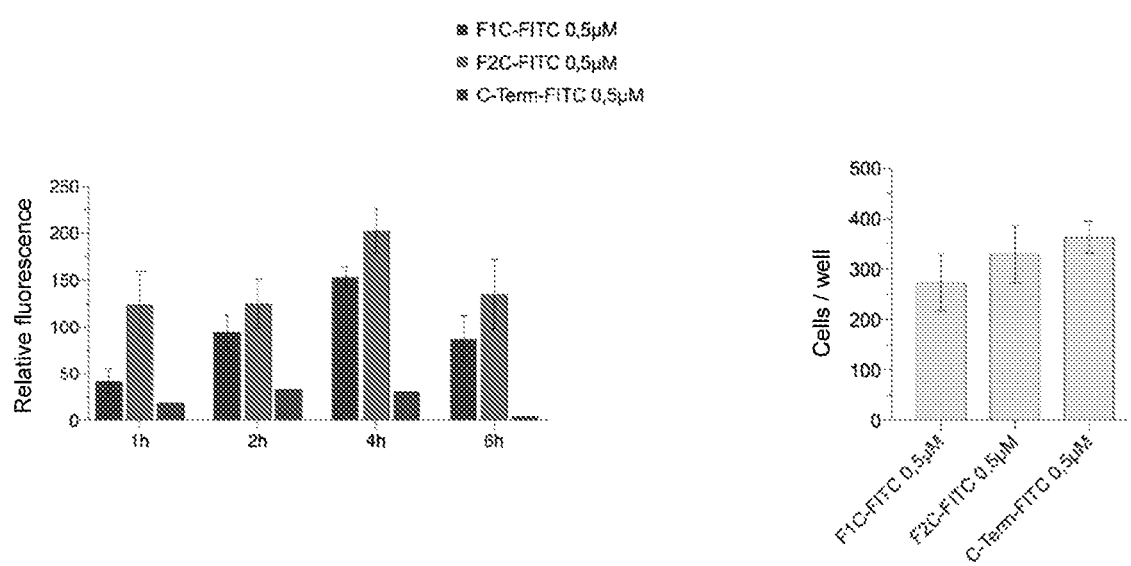
FIG. 15 shows the quantification of SK-Mel-28 cells incubated with F1C-FITC and F2C-FITC for 1 h, 2 h, 4 h and 6 h and evaluated by HCS. The quantification of the relative fluorescence product internalization of the F1C-FITC and F2C-FITC peptides in even shorter times at a concentration of 5 µM was performed, showing greater ease of internalization of the F2C-FITC peptide. This result is supported by the similar number of cells between treatments.

Given the fluorescence emission of each labeled peptide, it was decided to work with an intermediate concentration (5 µM) for further internalization assays. Thus, quantitative analysis of the fluorescence of F1C-FITC and F2C-FITC peptides in SK-Mel-28 cells was performed, demonstrating greater ease of internalization of F2C-FITC than F1C-FITC for 1, 2, 4 and 6 h of incubation (FIG. 15). This difference in fluorescence emission can be guaranteed by the close number of cells between the different treatments (FIG. 15), which supports the best result resulting from the internalization of the F2C-FITC peptide (FIG. 14).

Those skilled in the art will value the knowledge presented herein and may reproduce the invention in the presented embodiments and in other variants and alternatives, covered by the scope of the following claims.

The invention claimed is:

1. A compound comprising the peptide as defined in SEQ ID NO: 3 or SEQ ID NO:5, wherein the compound lacks a Kunitz domain, and wherein the compound is chemically bonded or fused to an active pharmaceutical ingredient other than a Kunitz domain.

2. The compound, of claim 1, wherein the compound is in cyclic, amidated, alkylated, alkoxylated, halogenated, hydroxylated or PEGylated form, or modified with other functional groups and/or with unnatural amino acids, wherein the unnatural amino acids optionally comprise D-forms of amino acids; salts thereof; or combinations thereof.

3. The compound of claim 1, wherein the pharmaceutically active ingredient is selected from: a compound for diagnostic use; a fluorophore; a small molecule; a polypeptide; an antineoplastic agent; or combinations thereof.

4. A pharmaceutical composition for the treatment of cancer comprising a pharmaceutically acceptable excipient and a compound according to claim 1.

5. A method for in vitro diagnosis of cellular and/or biochemical alterations comprising the steps of:
   (i) selecting one or more eukaryotic cells;
   (ii) contacting said cells with a compound according to claim 1, or a molecular entity comprising said compound, so that said compound penetrates said cell; and
   (iii) detecting/assessing the state of the cellular/biochemical alteration.

6. A method for diagnosing cellular and/or biochemical alterations comprising the steps of:
   (i) selecting one or more eukaryotic cells;
   (ii) contacting said cells with a compound according to claim 1, or a molecular entity comprising said compound, so that said compound penetrates said cell; and
   (iii) detecting/assessing the state of the cellular/biochemical alteration.

7. A method of treating cancer or related diseases comprising the application of a compound according to claim 1 in a patient.

8. A method of carrying and/or internalizing an active pharmaceutical ingredient other than a Kunitz domain into eukaryotic cells:
   administering the pharmaceutical composition of claim 4 in an in vivo or ex vivo eukaryotic cell or patient.

9. A method for preparing a drug comprising chemically binding or fusing one or more pharmaceutically active ingredients other than a Kunitz domain with a compound comprising the peptide as defined in SEQ ID NO:3 or SEQ ID NO:5, to generate a drug comprising the chemically bonded or fused compound.

10. The method of claim 9, wherein the pharmaceutically active ingredient is selected from: a compound for diagnostic use; a fluorophore; a small molecule; a polypeptide; an antineoplastic agent; or combinations thereof.

11. The method of claim 9, further comprising producing a pharmaceutical composition comprising said drug.

* * * * *